US008372953B2

(12) United States Patent
Bott et al.

(10) Patent No.: US 8,372,953 B2
(45) Date of Patent: Feb. 12, 2013

(54) COMPOSITION COMPRISING VARIOUS PROTEORHODOPSINS AND/OR BACTERIORHODOPSINS AND USE THEREOF

(75) Inventors: Richard R. Bott, Burlingame, CA (US); Rasmus B. Jensen, Hedehusene (DK); Bradley R. Kelemen, Menlo Park, CA (US); Donald E. Ward, II, Los Altos, CA (US); Gregory M. Whited, Belmont, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/181,387

(22) Filed: Jul. 12, 2011

(65) Prior Publication Data

US 2012/0010333 A1 Jan. 12, 2012

Related U.S. Application Data

(62) Division of application No. 11/569,862, filed as application No. PCT/US2005/020899 on Jun. 9, 2005, now Pat. No. 7,982,000.

(60) Provisional application No. 60/579,181, filed on Jun. 10, 2004, provisional application No. 60/622,424, filed on Oct. 26, 2004.

(51) Int. Cl.
*C07K 17/00* (2006.01)
*G03C 1/00* (2006.01)

(52) U.S. Cl. ........................... 530/350; 430/332

(58) Field of Classification Search .......... None
See application file for complete search history.

(56) References Cited

U.S. PATENT DOCUMENTS

| | | | |
|---|---|---|---|
| 5,346,789 A | 9/1994 | Lewis | |
| 5,470,690 A | 11/1995 | Lewis | |
| 6,140,012 A | 10/2000 | Smithey et al. | |
| 6,483,735 B1 | 11/2002 | Rentzepis | |
| 6,743,283 B2 | 6/2004 | Imanishi et al. | |
| 7,378,219 B2 | 5/2008 | Jensen et al. | |
| 2008/0290328 A1 | 11/2008 | Jensen et al. | |

FOREIGN PATENT DOCUMENTS

| | | |
|---|---|---|
| WO | WO 00/59731 | 10/2000 |
| WO | WO 2004/048451 A2 | 6/2004 |
| WO | WO 2004/063326 A2 | 7/2004 |
| WO | WO 2005/124230 A1 | 12/2005 |

OTHER PUBLICATIONS

Gartner et al. (Trends in Microb 11: 405-407, 2003).*
Fischer et al., "Biomolecular optical data storage and data encryption," IEEE Trans Nanobiosc, vol. 2, No. 1, pp. 1-5 (Mar. 2003).
Kelemen et al., "Proteorhodopsin in living color: diversity of spectral properties within living bacterial cells," Biochim Biophys Acta, vol. 1618, pp. 25-32 (2003).
Int'l Search Report, WO 2005/123110, mailed Oct. 26, 2007.
Venter, et al., "Environmental Genome Shotgun Sequencing of the Sargasso Sea," Science, vol. 304, pp. 66-74 (2004).
Hampp, "Bacteriorhodopsin: mutating a biomaterial into an optoelectronic material," Applied Microbiology and Biotechnology, vol. 53, pp. 633-639 (2000).
Gourevich, et al., "Multidye Nanostructured Material for Optical Data Storage and Security Labeling," Chemistry of Materials, vol. 16, No. 8, pp. 1472-1479 (2004).
Hampp, "Bacteriorhodopsin as a Photochromic Retinal Protein for Optical Memories," Chemical Reviews, vol. 100, No. 5, pp. 1755-1776 (2000).
Beja, "Bacterial Rhodopsin: Evidence for a New Type of Phototrophy in the Sea," Science, vol. 289, pp. 1902-1906 (2000).
Dioumaev, et al., "Proton Transfers in the Photochemical Reaction Cycle of Proteorhodopsin," Biocehmistry, vol. 41, pp. 5348-5358 (2002).
Dioumaev, et al., "Proton Transport by Proteorhodopsin Requires that the Retinal Schiff Base Counterion Asp-97 Be Anionic," Biochemistry, vol. 42, pp. 6582-6587 (2003).
Hampp, Norbert, et al., "Printing Inks Containing the Photochromic Protein Bacteriorhodopsin", Proceedings of the SPIE—The International Society for Optical Engineering, SPIE, vol. 3973, Jan. 1, 2000, pp. 118-125.
Min, Junhong, et al., "Visual information processing using bacteriorhodopsin-based complex LB films", Biosensors and Bioelectronics, vol. 16, No. 9-12, Dec. 2001, pp. 917-923.
Supplementary European Search Report for EP05761082, mailed Aug. 5, 2009.
Notice of Allowance for U.S. Appl. No. 11/569,864, mailed on Aug. 17, 2009.
Varo, Gyorgy, et al., "Characterization of the Photochemical Reaction cycle of Proteorhodopsin", Biophysical Journal, vol. 84, Feb. 2003, pp. 12020-12070.

* cited by examiner

*Primary Examiner* — Daniel E Kolker
*Assistant Examiner* — Aditi Dutt
(74) *Attorney, Agent, or Firm* — Perkins Coie LLP.; Viola T. Kung

(57) ABSTRACT

The present invention provides a solid material comprising an immobilized mixture of two or more proteorhodopsins, two or more bacteriorhodopsins, or one or more bacteriorhodopsin and one or more proteorhodopsins. The proteorhodopsins are selected from the group consisting of all-trans-retinal-containing proteorhodopsins and retinal analog-containing proteorhodopsins; all of which have absorption spectra that do not overlap. The bacteriorhodopsins are selected from the group consisting of all-trans-retinal-containing bacteriorhodopsins and retinal analog-containing bacteriorhodopsins; all of which have absorption spectra that do not overlap. The present invention also provides an optical information carrier, such as an optical data storage material and a fraud-proof optical data carrier, comprising the above-described solid material and a substrate selected from the group consisting of glass, paper, metal, fabric material, and plastic material, wherein said solid material is deposited on said substrate. The present invention further provides security ink comprising one or more hydrophilic polymers and a mixture of various photochromic materials.

10 Claims, 1 Drawing Sheet

COMPOSITION COMPRISING VARIOUS PROTEORHODOPSINS AND/OR BACTERIORHODOPSINS AND USE THEREOF

This application is a divisional application of U.S. application Ser. No. 11/569,862, filed Dec. 13, 2007, now U.S. Pat. No. 7,982,000; which is a National Stage of International Application PCT/US2005/020899, filed Jun. 9, 2005, published Dec. 29, 2005, under PCT Article 21(2) in English; which claims the priority of U.S. Provisional Application Nos. 60/579,181, filed Jun. 10, 2004, and 60/622,424, filed Oct. 26, 2004; the above-identified applications are incorporated herein by reference in their entireties.

FIELD OF INVENTION

The present invention relates to a solid material having an immobilized mixture of various photochromic materials having absorption spectra that do not overlap significantly. The various photochromic materials are all-trans-retinal-containing proteorhodopsins, retinal analog-containing proteorhodopsins, all-trans-retinal-containing bacteriorhodopsins and/or retinal analog-containing bacteriorhodopsins. Particularly, the invention relates to use of a mixture of various photochromic materials as optical data storage materials, fraud-proof optical data carriers, and security ink.

BACKGROUND OF THE INVENTION

Bacteriorhodopsin (BR) is a retinal protein molecule found in the photosynthetic system of a salt-marsh bacterium called *Halobacterium salinarium*. The BR molecules are located in the cell membrane, forming a 2D protein-lipid array, commonly called the purple membrane. The use of photochromic proteins like bacteriorhodopsin (BR) for optical data storage has been considered promising.

Proteorhodopsins (PRs) are distantly related to bacteriorhodopsin (BR) (22-24% sequence identity). Proteorhodopsins are integral membrane proteins; they are isolated from uncultivated marine eubacteria and function as light-driven proton pumps. Upon absorption of light by the all-trans-retinal co-factor, proteorhodopsin goes through a photocycle with a number of intermediates. It is believed that upon excitation of the proteorhodopsin molecule by light stimulation, a proteorhodopsin/retinal complex is excited to an unstable intermediate energy state. Proteorhodopsin progresses through a series of unstable energy states that can vary in terms of energy plateaus or intermediates, e.g., an "M-like state" or "M-state", a "K-like state" or "K-state", an "N-like state" or "N-state", or an "O-like state" or "O-state". Subsequently, the complex reverts to a more stable basal state concomitant with transport of a proton.

Béjà, et al. (*Science* 289:1902-6, 2000) disclose the cloning of a proteorhodopsin gene from an uncultivated member of the marine γ-proteobacteria (i.e., the "SAR86" group). The proteorhodopsin was functionally expressed in *E. coli* and bound all-trans-retinal to form an active light-driven proton pump.

Béjà, et al. (*Nature* 411:786-9, 2001) disclose the cloning of over twenty variant proteorhodopsin genes from various sources. The proteorhodopsin variants appear to belong to an extensive family of globally distributed proteorhodopsin variants that maximally absorb light at different wavelengths.

Dioumaev, et al. (Biochemistry, 42: 6582-6587 (2003)) disclose using proteorhodopsin-containing membrane fragments encased in polyacrylamide gel for flash photolysis and measurements of absorption changes in the visible range.

U.S. Pat. No. 5,235,076 (Asato) discloses azulenic retinoid compounds and therapeutic compositions. The compositions are useful in treating dermatological disorders such as acne and psoriasis.

U.S. Pat. No. 4,896,049 (Ogawa) discloses various synthetic analogs of retinal, which have different absorption wavelengths. The synthetic retinal analogs disclosed in Ogawa are incorporated herein by reference.

Khodonov, et al. (*Sensors and Actuators B* 38-39:218-221 (1997)) describe modified bacteriorhodopsin by replacing the natural bacteriorhodopsin chromophore, all-trans-retinal, with its analogs. The retinal analogs disclosed in Khodonov are incorporated herein by reference.

Imai, et al. (*Photochemistry and Photobiology*, 70: 111-115 (1999)) disclose that azulenic retinal analogs failed to yield a red-shifted visual pigment analog, whereas the 9-cis isomers of the polyenals 3-methoxy-3-dehydroretinal and 14F-3-methoxy-3-dehydroretinal yielded iodopsin pigment analogs at 663 and 720 nm.

U.S. Pat. No. 6,483,735 (Rentzepis) discloses a three- or four-dimensional radiation memory that serves to store multiple binary bits of information in the same physical volumes of each of a multiplicity of addressable domains in each of potentially multiple layers within the entire volume of a planar disc, or in a random-access volume radiation memory. The storage of multiple information bits within the same addressable domains is done by the co-location of several different florescent chemical compounds in the volume of each such domain; the florescent chemical compounds are not rewriteable.

U.S. Pat. Nos. 5,470,690 and 5,346,789 (Lewis) disclose a stable, image-retaining, optically switchable film containing bacteriorhodopsin obtained from *Halobacterium Halobium* (currently known as *Halobacterium salinarum*) in a high-pH polyvinyl alcohol solution for an optical memory for data storage.

Gourevich, I. et al. (*Chemical Materials*, Multidye Nanostructured Material for Optical Data Storage and Security Labeling (2004)) disclose a polymer nanocomposite for three-dimensional optical data storage and security labeling using visible and near-IR fluorescent dyes. The data is written via selective photobleaching of the fluorescent dyes, which are not rewriteable.

Optical data storage has the potential to revolutionize the computer industry, since optical data storage provides both a very high storage capacity and rapid reading and writing of data. Additionally, optical signal processing could be used in a highly parallel fashion for pattern recognition, which is difficult to do with the current computing technologies. A functional optical material with low light scattering, large data storage capacity, and rewriteable capacity is required for these applications to succeed.

Documents like banknotes, checks, identity cards, etc. often incorporate security features to make them difficult to copy or counterfeit. Most of these are based on either using special paper with security features like watermarks incorporated during paper manufacturing, or printing hairline patterns that are difficult to copy. However, such features are permanently visible and do not meet sophisticated security requirements.

There are needs for optical information carriers that can be produced efficiently and economically and have low background noise (crosstalk), large data storage capacity, and rewriteable capacity. Such optical information carriers are effective as optical data storage material or fraud-proof optical data carriers.

SUMMARY OF THE INVENTION

The present invention provides a solid material comprising an immobilized mixture of photochromic materials that have absorption spectra that do not overlap significantly among each other. The photochromic materials comprise two or more proteorhodopsins, two or more bacteriorhodopsins, or one or more bacteriorhodopsin and one or more proteorhodopsins. The proteorhodopsins are selected from the group consisting of all-trans-retinal-containing proteorhodopsins and retinal analog-containing proteorhodopsins. The bacteriorhodopsins are selected from the group consisting of all-trans-retinal-containing bacteriorhodopsins and retinal analog-containing bacteriorhodopsins. The solid material preferably comprises one or more hydrophilic polymers that are capable of forming a homogeneous phase with said photochromic materials prior to solidification to a solid form.

The present invention provides an optical information carrier comprising the solid material as described above, wherein data are written differentially by actinic light (writing light) of various wavelengths and/or optical signals are read differentially by reading light of various wavelengths. The optical signals can be read differentially by determining the decrease of B-state molecules of each photochromic material. Alternatively, the optical signals can be read differentially by determining the light absorbance at maximum absorption wavelength of the M-state, or other excited state, by each photochromic material. The various photochromic materials provide non-destructive writing and reading of data and are capable of being reused. The optical information carrier further comprises a substrate selected from the group consisting of glass, paper, metal, fabric material, and plastic material, wherein the solid material is deposited on said substrate. The optical information carrier of the present invention is, for example, a fraud-proof optical data carrier or an optical data storage material.

The present invention further provides security ink comprising different proteorhodopsins and/or bacteriorhodopsins as described above and one or more hydrophilic polymers, wherein said different proteorhodopsins and/or bacteriorhodopsins and the hydrophilic polymers form a homogeneous liquid phase, said ink solidifies or dries after application onto a surface, thereby immobilizing said various photochromic materials onto a specific location where the ink is applied.

DETAILED DESCRIPTION OF THE INVENTION

Definitions

Figure 1:
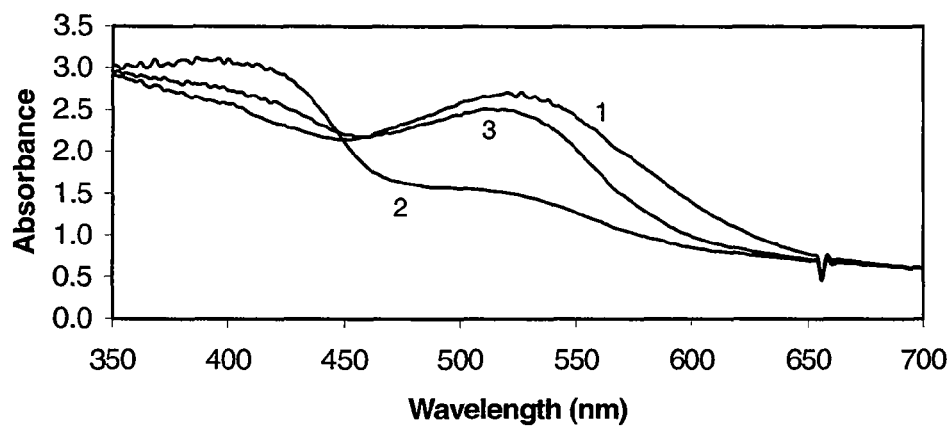
FIG. 1 shows the temporary data storage spectra of a mixture of bacteriorhodopsin and proteorhodopsin immobilized in a transparent matrix. The spectra were recorded in sequence as described. Spectrum 1 was taken after the mixture was illuminated with a violet light (400 nm). Spectrum 2 was taken after the mixture was illuminated with a green light (510 nm). Spectrum 3 was taken after the mixture was illuminated with a violet light (400 nm), followed by a red light (640 nm).

As used herein, the term "actinic light" refers to radiant energy, especially in the visible and ultraviolet spectral regions, which can produce photochromic changes in a photochromic material.

As used herein, the term "apoprotein" refers to the protein part of a conjugated protein. A "proteorhodopsin or bacteriorhodopsin apoprotein" refers to the proteorhodopsin or bacteriorhodopsin protein itself without the all-trans-retinal or retinal analog.

As used herein, the term "azulenic retinoid compound" refers to a compound having azulenic group attached to a modified or non-modified all-trans-retinal backbone.

As used herein, the term "basal state" or "B-state" or "B-like state" refers to the basal state of the photocycle of a proteorhodopsin molecule or a bacteriorhodopsin molecule without light excitation. The term "M-state" or "M-like state" refers to an excited spectral state in a photocycle as compared with the basal state.

As used herein, "photochromic" refers to having the capability to change color upon exposure to radiant energy (as light).

As used herein, the term "retinal analog" refers to a compound that replaces all-trans retinal and is capable of coupling with the apoprotein of a proteorhodopsin or a bacteriorhodopsin.

The present invention provides a solid material comprising an immobilized mixture of various photochromic materials, wherein said various photochromic materials all have absorption spectra that do not overlap significantly.

The solid material of the present invention comprises one or more hydrophilic polymers that are capable of forming a homogeneous phase with said various photochromic materials prior to solidification to a solid form. The solid material that contains a mixture of various photochromic materials is useful as optical information data carrier such as an optical data storage material and fraud-proof optical data carrier. The various photochromic materials, which have absorption spectra that do not overlap significantly, provide an increased capacity of optical data storage and allow for parallel processing. The solid material is useful in storing (writing) optical data. The material is capable of retaining data, permits nondestructive detection (reading) of such data, and is reusable after optical erasure of data.

In one embodiment, the photochromic material that has changed color has the ability to return to the original color. Return to the original color by the photochromic material can be spontaneous or caused by re-exposure to radiant energy.

Various photochromic materials of the present invention include various proteorhodopsins and/or bacteriorhodopsins; all of which have absorption spectra that do not overlap significantly. By "not overlap significantly," it is meant that a particular wavelength can be selected such that the absorbance (optical density) at that wavelength of one proteorhodopsin or bacteriorhodopsin is at least 2, at least 3, at least 4, at least 5, at least 6, at least 7, at least 8, at least 9, or at least 10 times higher than the absorbance of the other proteorhodopsin or bacteriorhodopsin under the same conditions (e.g. temperature). For example, at a selected wavelength such as 600 nm, if photochromic composition X has an absorbance of 1.0 OD, and photochromic composition Y has an absorbance equal to or less than 0.5, preferably 0.33, preferably 0.2, more preferably 0.1 OD, then the absorbance spectra of photochromic compositions X and Y do not overlap significantly.

In one embodiment of the invention, various photochromic materials comprise two or more (e.g. three, four, five, six, seven, eight, etc.) proteorhodopsins. In another embodiment of the invention, various photochromic materials comprise two or more bacteriorhodopsins (e.g. three, four, five, six, seven, eight, etc.). In yet another embodiment of the invention, various photochromic materials comprise one or more bacteriorhodopsins and one or more proteorhodopsins. In the present invention, the proteorhodopsins are selected from the group consisting of all-trans-retinal-containing proteorhodopsins and retinal analog-containing proteorhodopsins. The bacteriorhodopsins are selected from the group consisting of all-trans-retinal-containing bacteriorhodopsins and retinal analog-containing bacteriorhodopsins.

Proteorhodopsins

Proteorhodopsin is a trans-membrane protein with a structure of seven lipid membrane-spanning α-helices that form a generally cylinder shaped channel. When folded correctly and supplied with all-trans-retinal, the seven α-helices of proteorhodpsin are arranged as a cage surrounding the all-trans-retinal. One advantage of using proteorhodopsins in an optical information carrier is that proteorhodopsins can be functionally expressed in *E. coli* to produce a large quantity (grams or kilograms) of protein economically and efficiently. The proteorhodopsin-expressing cells are lysed and the pellets containing the membrane fraction are collected. The proteorhodopsin protein can be further extracted from the membrane by detergent solubilization. Either the membranes or fragments of membranes that contain proteorhodopsins, or the purified proteorhodopsin proteins can be used as an optical information carrier such as an optical data storage material or a fraud-proof optical data carrier.

When using proteorhodopsins as an optical data storage material, it is desirable to immobilize detergent-solubilized proteorhodopsins to avoid light scattering. In one embodiment of the invention, detergent-solubilized and membrane-free proteorhodopsins are used. Detergent-solubilized proteorhodopsins are usually in the form of a monomer, and sometimes in the form of an oligomer (dimer, trimer, tetramer, pentamer, or hexamer). Individual proteorhodopsin monomers are about 5 nm in size; such small size does not cause scattering of light in the visible range. The monomeric or oligomeric stability of proteorhodopsin makes it desirable as a component of an optical data storage material without having the problem of a μm-sized particle that scatters light. Additionally, the small size of the individual proteorhodopsin monomers makes it easier to obtain a uniform protein distribution in the optical data storage material.

Different from bacteriodopsins, proteorhodopsins are stable in its monomeric or oligomeric state for at least one month at room temperature, or one year at 4° C. The term "stable" refers to that proteorhodopsin does not change its spectral property significantly (less than 30 nm in maximum absorption wavelength) and is able to produce a photocycle upon excitation by light that includes a transition from the basal state to the M-state.

The basal absorption maxima of all-trans-retinal-containing proteorhodopsin variants are in general between 480 nm and 550 nm, often between 488 and 526 nm. (Man, et al. Embo J. 22:1725-1731 (2003))

The absorption maxima of the M-state of proteorhodopsins in general are between 350 nm and 450 nm, often about 410 nm. The M-state is distinguished from other identified spectral states, the K-, N- and O-like states, which all have red-shifted absorption spectra (e.g. >530 nm) compared with the basal state.

When a proteorhodopsin molecule is exposed to actinic light of an excitation wavelength, it is excited to an activated M-state and changes to a yellow color. The color is reverted to its basal color either spontaneously with time or by exposing the material to a second light. For example, the proteorhodopsin-containing material is excited by a yellow light or a green light to change color from red or purple to yellow; the color change is erased spontaneously or by illuminating the material with purple or blue light. The excitation and erasing cycle can be repeated many times, thus, the proteorhodopsin molecule is re-usable.

Proteorhodopsins useful for the present invention can be derived from any naturally occurring proteorhodopsin. Various natural nucleic acid sequences, encoding various natural proteorhodopsins, have been obtained from naturally occurring members of the domain bacteria. Such members include marine bacteria, such as bacteria from the SAR86 group. The natural nucleic acid sequences of proteorhodopsins are cloned and the natural form of proteorhodopsins is expressed. There are many natural forms of proteorhodopsins; including those derived from marine bacteria and those derived from non-marine bacteria; all of which can be used for the present invention.

For example, natural forms of proteorhodopsins include Hot75m1, Bac31A8, Bac40E8, Bac41B4, Bac64A5, Hot0m1, Hot75m3, Hot75m4, Hot75m8, MB0m1, MB0m2, MB20m2, MB20m5, MB20m12, MB40m1, MB40m5, MB100m5, MB100m7, MB100m9, MB100m10, PalB1, PalB2, PalB5, PalB7, PalB6, PalB8, PalE1, PalE6, PalE7, MED 26, MED27, MED36, MED101, MED102, MED106, MED25, MED202, MED204 MED208, REDA9, REDB9, REDF9, RED19, RED2, RED23, RED27, RED30, RED4, RED5, REDr6a5a14, REDr6a5a6, REDr7__1__4, REDs3__7, REDr7__1__15, REDs3__15, medA15r8ex6, REDr7__1__16, medA15r11b9, medA15r9b5, medA15r8b3, medA15r11b3, medA15_r8__1, medA17R9__1, medA15r8b9, medA19_R8__16, medA19_R8__19, medA17_R8__6, medA15r9b7, medA15_R8__3, medA15r10b5, medA19_r9__9, medA15_r8ex7, medA19_R8__20, medA15_R8ex9, medA15_r9__3, medA17_r8__15, medA17_r8__11, medA15r8b8, medA15r8ex4, ANT32C12 PR and HOT2C01 PR. See Baja, et al., *Nature* 411:786-9 (2001); Man, et al., *EMBO J.*, 22:1725-1731 (2003); and Sabehi, et al., *Environ. Microbiol.*, 5: 842-9 (2003). The nucleotide and amino acid sequences of the above various proteorhodopsins have been deposited with Genbank under accession numbers AF349976-AF350003, AF279106, AY210898-AY210919, AY250714-AY250741, AY372453 and AY372455. In addition, Venter, et al. (*Science* 304: 66-74 (2004)) recently have reported 782 new rhodopsin analogs, most of which are proteorhodopsins, found in the Sargasso Sea. The proteorhodopsins described in the above references are suitable for the present invention.

Proteorhodopsins useful for the present invention can also be derived from any non-naturally occurring proteorhodopsins, such as proteorhodopsin mutants. The term "proteorhodopsin mutant" refers to a proteorhodopsin comprising one or more mutations that insert, delete, and/or substitute one or more amino acid residues and/or nucleotides from the natural sequences of proteorhodopsins. For example, the nucleotide sequence can be altered by a substitution of a different codon that encodes the same or a functionally equivalent amino acid residue within the sequence, thus producing a silent change. For example, an amino acid residue within the sequence can be substituted by another amino acid of a similar polarity, or a similar class. Non-polar (hydrophobic) amino acids include alanine, leucine, isoleucine, valine, proline, phenylalanine, tryptophan, glycine and methionine. Polar neutral amino acids include serine, threonine, cysteine, tyrosine, asparagine, and glutamine. Positively charged (basic) amino acids include arginine, lysine, and histidine. Negatively charged (acidic) amino acids include aspartic and glutamic acid.

Proteorhodopsin mutants useful for the present invention, for example, include the amino acid sequence of Bac31A8 H75K, Bac31A8 H75N, Bac31A8 H75Q, Bac31A8 E108Q, Bac31 A8 D97N, Hot75ml H77K, Hot75ml H77N, Hot75ml H77Q, Hot75ml H77E, Hot75ml H77D, Hot75ml H77W, Hot75ml R96A, Hot 75ml E110Q, Hot75ml D99N, Hot75ml R96E, and Hot75ml R96Q. In which, Bac31A8 H75K means that the 75 amino residue of the naturally occurring Bac31A8 is mutated from histine to lysine. Proteorhodopsin mutants have been disclosed in the co-pending U.S. Application Publication No. 2005-0095605; which is incorporated herein by reference in its entirety.

Bacteriorhodopsins

Bacteriorhodopsin (BR) is an all-trans-retinal-containing protein molecule found in the photosynthetic system of a salt-marsh bacterium called *Halobacterium salinarium*. BR-based optical films have been worked on for the past two decades, but by themselves, these films do not have the required properties to make them commercially viable for data storage applications. One of the problems with the BR-based films is that BR forms 0.2-1 µm sized protein-lipid patches. If BR is extracted from these patches to form a monomeric protein, it becomes unstable and is inactivated in a few days. The problem with using these BR patches in optical films is that the patches are approximately the same size as the wavelength of the light used to interface with the film, which results in significant light scattering during read and write cycles, thereby increasing noise and degrading the performance of the film. Additionally, the BR patches tend to stick to each other, which result in uneven distribution of the BR protein in the film, and further degrade the performance of BR-based optical films.

Another disadvantage of BR in comparison with PR is that BR is expensive to produce in a large quantity. BR has to be expressed in its natural organism *H. salinarum* for it to be fully functional (Dunn, et al., *J Biol Chem*, 262: 9246-9254 (1987); Hohenfeld, et al., *FEBS Lett*, 442: 198-202 (1999)). *H. salinarum* grows very slowly, gives a low cell density and requires the presence of large amounts of salt in the growth medium. The low productivity of *H. salinarum* and the need for expensive custom-made fermentation and recovery equipment that can tolerate the high salt growth medium result in high cost of BR production.

Nonetheless, bacteriorhodopsin has a unique maximum absorbance wavelength of 590 nm, which is different from those of most proteorhodopsins, and is thus useful as a component of the various photochromic materials. BR molecules are useful when combined in a material consisting of PR molecules.

The basal absorption maxima of all-trans-retinal-containing bacteriorhodopsins are in general 590 nm, without any significant variation. All-trans-retinal-containing bacteriorhodopsins all have the similar purple color. The absorption maxima of the M-state of bacteriorhodopsins in general are about 410 nm.

When bacteriorhodopsin is exposed to light of excitation wavelength, it is excited to an activated M-state and changes to yellow color. The color is reverted to its basal color either spontaneously with time or by exposing the material to a second light. For example, the bacteriorhodopsin-containing material can be excited by a green light to change color from purple to yellow; the color change is erased spontaneously or by illuminating the material with blue light.

Bacteriorhodopsins useful for the present invention can be derived from any naturally occurring bacteriorhodopsins. Bacteriorhodopsins useful for the present invention can also be derived from any non-naturally occurring bacteriorhodopsins, such as bacteriorhodopsin mutants. The term "bacteriorhodopsin mutant" refers to a bacteriorhodopsin comprising one or more mutations that insert, delete, and/or substitute one or more amino acid residues and/or nucleotides from the natural amino or nucleic acid sequence of bacteriorhodopsin. For example, the nucleotide sequence can be altered by a substitution of a different codon that encodes the same or a functionally equivalent amino acid residue within the sequence, thus producing a silent change. For example, an amino acid residue within the sequence can be substituted by another amino acid of a similar polarity, or a similar class. Non-polar (hydrophobic) amino acids include alanine, leucine, isoleucine, valine, proline, phenylalanine, tryptophan, glycine and methionine. Polar neutral amino acids include serine, threonine, cysteine, tyrosine, asparagine, and glutamine. Positively charged (basic) amino acids include arginine, lysine, and histidine. Negatively charged (acidic) amino acids include aspartic and glutamic acid.

Bacteriorhodopsin mutants useful for the present invention include: BR-D85N and BR-D96N, (Hampp, *Chem. Rev.*, 100: 1755-1776 (2000)), BR-T90V, BR-D115L, BR-V49A (Dioumaev, et al., *Biochemistry* 41(17):5348-58 (2002)), BR-E194C (Balashov, et al., *Biochemistry* 36:8671-8676 (1997)), BR-E194Q and BR-E204Q (Dioumaev, et al., *Biochemistry* 37:2496-2506 (1998)), BR-R82A and BR-D85E (Subramaniam, et al., *Proc. Natl. Acad. Sci. U.S.A.*, 87:1013-1017 (1990)), BR-D85A, BR-D85N, BR-D85E, BR-D212N, BR-D212E, BR-R82A, BR-R82Q, BR-D115A, BR-D115N, BR-D115E, BR-D96A, BR-D96N, BR-D96E (Otto, et al., *Proc. Natl. Acad. Sci. U.S.A.* 87:1018-1022 (1990)), BR-E204Q, BR-E204D, BR-L93M, BR-L93T, BR-L93S (Kandori, et al., *Biochemistry* 36:5134-5141 (1997)), BR-V49A (Brown, et al., *Biochemistry* 33:12001-12011 (1994)), BR-L93A (Delaney, et al., *J. Phys. Chem. B.*, 101: 5619-5621 (1997)), as well as other possible bacteriorhodopsin mutants. In which, BR-D85N means that the 85 amino acid residue of the naturally occurring bacteriorhodopsin is mutated from aspartic acid (D) to asparagine (N).

Retinal Analogs

Various retinal analogs are useful in the present invention. In one embodiment, the retinal analog is an azulenic retinoid compound. In another embodiment, the retinal analog is a compound that is structurally similar to all-trans-retinal. A proteorhodopsin/bacteriorhodopsin apoprotein and a retinal analog form a photochromic material having spectral properties different from a corresponding photochromic material comprising the same proteorhodopsin/bacteriorhodopsin apoprotein and all-trans-retinal.

In one embodiment of the application, a proteorhodopsin/bacteriorhodopsin apoprotein and a retinal analog form a photochromic material, whose absorbance spectrum does not overlap significantly from the absorbance spectrum of a corresponding photochromic material comprising the same proteorhodopsin/bacteriorhodopsin apoprotein and all-trans-retinal under the same condition (e.g. temperature). In another embodiment of the application, a proteorhodopsin/bacteriorhodopsin apoprotein and retinal analog form a photochromic material that yields a red-shifted visual chromophore compared with a photochromic material comprising the same proteorhodopsin/bacteriorhodopsin apoprotein and all-trans-retinal under the same condition (e.g. temperature). The changes in spectral properties provide the use of multiple wavelengths of light to increase capacity of optical data storage and allow parallel processing.

The structure of all-trans-retinal is shown as following:

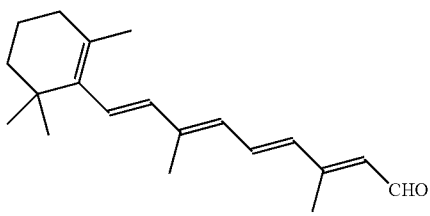

All-trans retinal

Retinal analogs useful for the present invention include azulenic retinoid compounds of Formula I:

Formula I

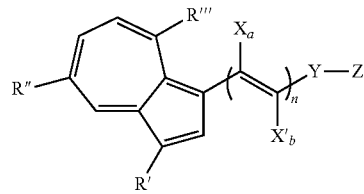

wherein R', R" and R'" are each independently H, $C_{1-4}$ straight chain alkyl, or $C_{1-4}$ branched chain alkyl, n is an integer from 1 to 4;

$X_a$ and $X'_b$ are each independently H, $C_{1-4}$ alkyl, F, Cl or $CF_3$;

Y is absent, or Y is a para-, meta-, or ortho-phenyl; and

Z is CHO.

In one embodiment of the invention, R', R" and R'" are independently H, methyl, isopropyl.

Preferably, R'=R'"=methyl, R"=isopropyl.

In a preferred embodiment of the invention, Y is absent.

The preparation of azulenic retinoid compounds is disclosed, for example, in U.S. Pat. No. 5,235,076 (Asato), which is incorporated herein by reference in its entirety.

Specific examples of Formula I that are useful for the present invention include the following compounds:

Compound A

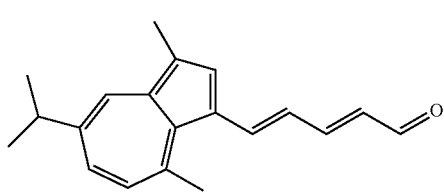

Compound B

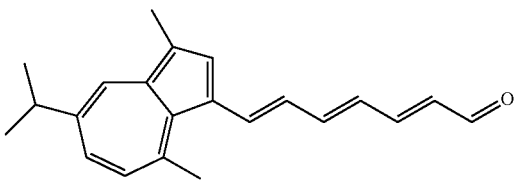

Compound C

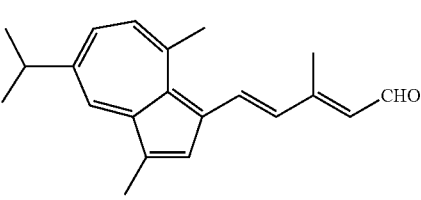

Compound D

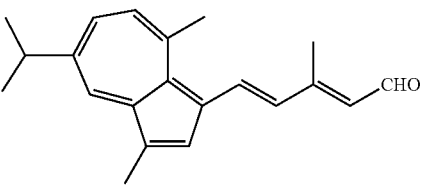

Compound E

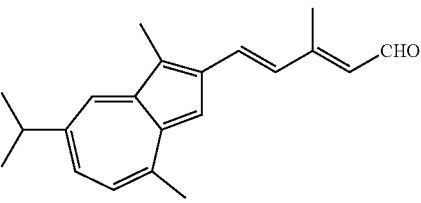

Compound F

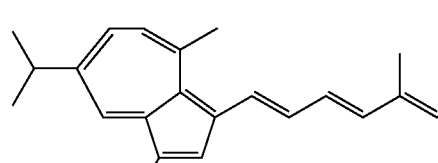

Compound G

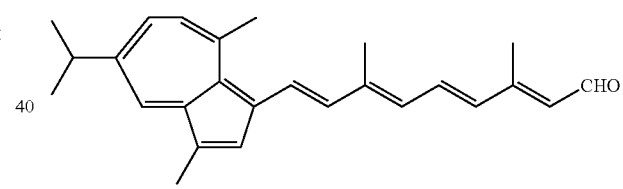

Compound H

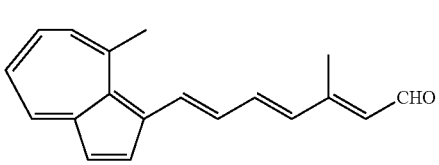

Compound I

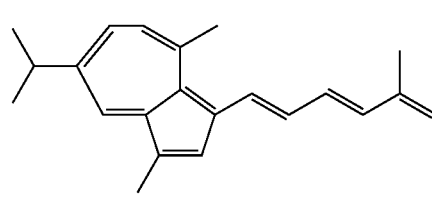

-continued

Compound J
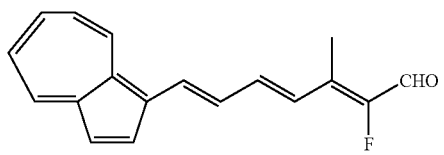

Compound K
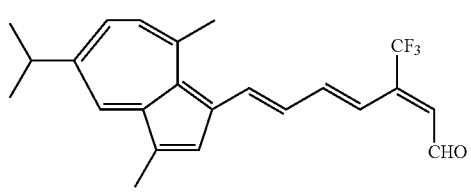

Compound L
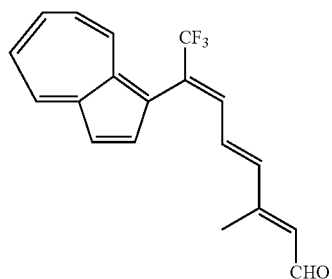

Compound M
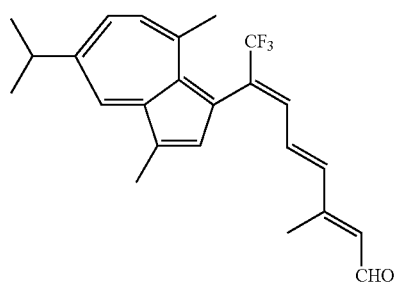

Compound N
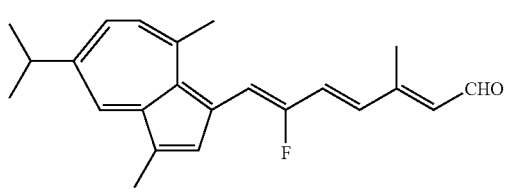

The retinal analogs useful for the present invention also include the following non-azulenic compounds that are structurally similar to all-trans-retinal:

Compound O
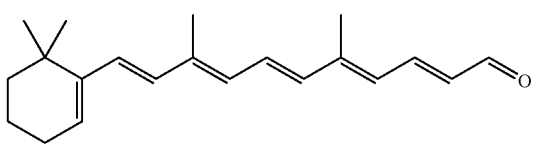

(U.S. Pat. No. 4,896,049 (Ogawa))

Compound P
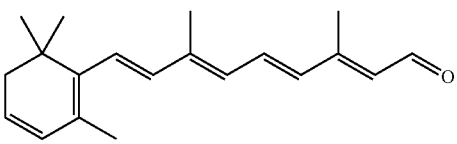

(U.S. Pat. No. 4,896,049 (Ogawa))

Compound Q
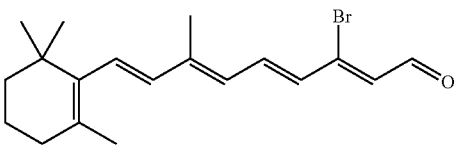

(U.S. Pat. No. 4,896,049 (Ogawa))

Compound R
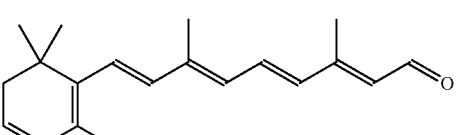

Khodonov, et al. (*Sensors and Actuators B* 38-39;218-221 (1997))

Compound S
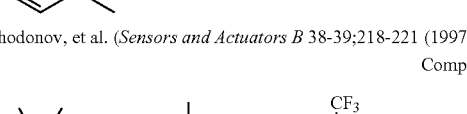

Khodonov, et al. (*Sensors and Actuators B* 38-39;218-221 (1997))

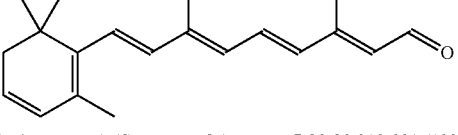

P-dimethyl aminocinnamaldehyde (DMCA)

DMCA is commercially available, for example, from Fluka AG (Buchs, Switzerland) through Sigma-Aldrich (St. Louis, Mo.), The Lab Depot, Inc. (Alpharetta, Ga.) and The Science Lab.Com (Kingwood, Tex.).

The retinal analog-containing proteorhodopsin can be conveniently prepared by expressing proteorhodopsin in the presence of the analog in a host cell. *E. coli*, for example, is an effective host cell because it does not produce all-trans-retinal. Other host cells, in which the synthetic pathway of all-trans-retinal is blocked, can also be effective host cells for preparing the retinal analog-containing proteorhodopsins. The analog is added to the cell culture and inserted into the proteorhodopsin protein during host cell growth and proteorhodopsin expression.

The retinal analog-containing bacteriorhodopsin, on the other hand, cannot be prepared conveniently by adding the analog during the expression of bacteriorhodopsin in its host cell *H. salinarum*. all-trans-retinal is produced by *H. salinarum*, and the all-trans-retinal-containing bacteriorhodopsin is formed during the expression of bacteriorhodopsin. In order to prepare retinal analog-containing bacteriorhodopsin, the all-trans-retinal needs to be removed from the all-trans-retinal-containing bacteriorhodopsin, then the retinal analog is added to the bacteriorhodopsin apoprotein to form a complex of bacteriorhodopsin and retinal analog.

A Solid Material Comprising a Mixture of Immobilized Proteorhodopsin and/or Bacteriorhodopsin The present invention provides a solid material comprising an immobilized mixture of one or more bacteriorhodopsins and one or more proteorhodopsins; preferably, all of the bacteriorhodopsins and proteorhodopsins have absorption spectra that do not overlap significantly. The present invention also provides a solid material comprising an immobilized mixture of two or more proteorhodopsins, which have absorption spectra that do not overlap significantly. The present invention additionally provides a solid material comprising an immobilized mixture of two or more bacteriorhodopsins, which have absorption spectra that do not overlap significantly. In the above solid materials, the proteorhodopsins are selected from the group consisting of all-trans-retinal-containing proteorhodopsins and retinal analog-containing proteorhodopsins, and the bacteriorhodopsins are selected from the group consisting of all-trans-retinal-containing bacteriorhodopsins and retinal analog-containing bacteriorhodopsins.

The solid material of the present invention preferably comprises one or more hydrophilic polymers that are capable of forming a homogeneous phase with proteorhodopsins and/or bacteriorhodopsins prior to solidification to a solid form such that the proteorhodopsins and/or bacteriorhodopsins are evenly distributed in the solid. By "homogeneous" is meant that the proteorhodopsins and/or bacteriorhodopsins and the hydrophilic polymer or its precursor form a uniform structure or composition throughout the mixture. As used herein, by "immobilized" is meant that proteorhodopsin/bacteriohodopsin is not mobile, and is fixed within the material. The interaction between proteorhodopsin and the material can be covalent or non-covalent. For example, proteorhodopsin/bacteriohodopsin can be physically entrapped within the material. Proteorhodopsin can also bind to the material by electrostatic charges, H-bond, hydrophobic, hydrophilic, or van der Waals interaction. By immobilization, the proteorhodopsin/bacteriohodopsin molecules are fixed and do not diffuse or diffuse very slowly within the solid material, such that an optical signal is not lost by diffusion of the proteorhodopsin molecules.

The hydrophilic polymers produce a non-opaque or optically transparent solid material, which allows efficient light excitation of the photochromic material contained therein.

Hydrophilic polymers suitable for this invention include silica sol gel, gelatin, polyacrylamide, acacia, agar, calcium carrageenan, calcium alginate, sodium alginate or other salts of alginic acid, algin, agarose, collagen, methyl cellulose, polyethylene glycol, sodium carboxy methyl cellulose, polyacrylic acid, partially cross-linked polyacrylic acid, hydroxyethyl cellulose, hydroxypropyl cellulose, hydroxypropylmethyl cellulose, polyethylene oxide, pectin and mixtures thereof.

Vinyl polymers and derivatives thereof are also useful in the present invention. Polyvinyl alcohol (PVA), is defined as a homopolymer or copolymer, in which vinyl acetate is a starting monomer unit and in which most or all (70-100%) of the acetate moieties are subsequently hydrolyzed to alcohol moieties. Other vinyl polymers useful in the present invention include, but are not limited to, polyvinyl acetate and polyvinyl pyrrolidone. Copolymers such as PVA-methylmethacrylate copolymer may also be used in the present invention. PVA is commercially available in a wide range of molecular weights, viscosities and varying degrees of hydrolysis from the polyvinyl acetate precursor.

Other polymers useful for this invention include polymers that form hydrogels such as Carbopol®, acidic carboxy polymers; Cyanamey-O polyacrylamides; cross-linked indene-maleic anhydride polymers, Polyox® polyethylene oxide polymers; starch graft copolymers; Aqua-Keepso acrylate polymer polysaccharides composed of condensed glucose units such as diester cross-linked polyglucan, and the like. Representative polymers that form hydrogel are shown in U.S. Pat. Nos. 3,865,108; 4,002,173; 4,207,893; and in Handbook of Common Polymers, by Scott and Roff, published by the Chemical Rubber Company, Cleveland, Ohio.

A solid material containing an immobilized mixture of various proteorhodopsin(s) and/or bacteriorhodopsin(s) in a hydrophilic polymer or in a mixture of hydrophilic polymers can be prepared by the steps of first mixing a hydrophilic polymer or its precursor with various proteorhodopsin(s) and/or bacteriorhodopsin(s) in water or an aqueous buffer to form a homogeneous solution, then solidifying the polymer, wherein the various proteorhodopsin and/or bacteriorhodopsin molecules are immobilized in the polymer. The solidification of the polymer is carried out by drying, cooling, curing, or polymerization.

For example, a polyvinyl alcohol material containing an immobilized mixture of various proteorhodopsin and/or bacteriorhodopsin molecules can be prepared by the method comprising the steps of: (a) mixing polyvinyl alcohol, water or a buffer having pH between about 3-12, and various proteorhodopsin and/or bacteriorhodopsin molecules to form a solution; (b) spreading the solution on the surface of a solid; and (c) drying the solution to form a polyvinyl alcohol material containing immobilized various proteorhodopsin and/or bacteriorhodopsin molecules A polyacrylamide material that contains immobilized various proteorhodopsin and/or bacteriorhodopsin molecules can be prepared by the method comprising the steps of (a) mixing acrylamide, bisacrylamide, various proteorhodopsin and/or bacteriorhodopsin molecules, and one or more polymerization initiators in water or a buffer having pH between 3-12; and (b) polymerizing acrylamide gel; whereby the various proteorhodopsin and/or bacteriorhodopsin molecules are immobilized within the polyacrylamide gel matrix. The polymerization initiators commonly used include ammonium persulfate and N,N,N',N'-tetramethylethylenediamine (TEMED). Alternatively, the method comprises the steps of (a) mixing acrylamide, bisacrylamide, various proteorhodopsin and/or bacteriorhodopsin molecules, and one or more UV-activated free radical generators in water or a buffer having pH between 3-12; and (b) exposing the mixture to UV light to polymerize acrylamide gel. The UV-activated free radical generators include riboflavin and TEMED (used together), 2,2-Dimethoxy-2-phenyl acetophenone (DMPA), and those described in the SE96047-3 patent.

Sol-gels that contain immobilized various proteorhodopsin and/or bacteriorhodopsin molecules can be prepared by the method comprising the steps of: (a) adding to a silane precursor an acidic solution having pH 1.5-4 to hydrolyze the silane precursor to form silicate sol; (b) adding to the silicate sol an aqueous solution containing various proteorhodopsins and/or bacteriorhodopsins at pH about 5-9; and (c) incubating (b) to form a gel; whereby the various proteorhodopsin and/or bacteriorhodopsin molecules are immobilized within the sol gel matrix. The silane precursors include tetraalkylorthosilicate, alkyltrialkoxysilane, aryltrialkoxysilane, dialkyldialkoxysilane, diaryldialkoxysilane, alkali metal silicate, polyol silicate, polyol siloxane, poly(methyl silicate), and alcohol-free poly(silicic acid). Preferred silane precursors are tetraalkylorthosilicate and poly(glyceryl)silicate.

Gelatin that contains immobilized various proteorhodopsins and/or bacteriorhodopsins can be prepared by the method comprising the steps of: (a) heating and dissolving gelatin in water or a buffer to form a homogeneous aqueous gelatin solution; (b) cooling the gelatin solution to about 39-45° C.; (c) mixing the cooled gelatin solution with various proteorhodopsins and/or bacteriorhodopsins; and (d) incubating (c) to form a gel; whereby the various proteorhodopsins and/or bacteriorhodopsins are immobilized within the gelatin gel matrix.

The solid material of the present invention contains an immobilized mixture of various proteorhodopsin and/or bacteriorhodopsin molecules. The various proteorhodopsin and/or bacteriorhodopsin molecules are pre-mixed prior to solidification to a solid form. Because the various proteorhodopsin and/or bacteriorhodopsin molecules are mixed in a molecular level, they are able to locate within the same addressable domains. This provides an economic procedure to produce various photochromic materials, which can be independently written and read, within the same addressable domains.

Technical Application

The proteorhodopsins and/or bacteriorhodopsins of the present invention have many technical applications. For example, they can be incorporated into instruments or devices having photochromic applications, photoelectric applications, and/or phototransport applications.

Under photochromic applications, proteorhodopsins and/or bacteriorhodopsins can be used for its light absorption properties for optical data storage, interferometry and/or photonics. Photochromic applications include, but are not limited to, holographic film. The retinal analog-containing proteorhodopsins can be used for optical data storage devices, such as 2-D storage, 3-D storage, holographic storage, associative storage, or the like. The retinal analog-containing proteorhodopsins can be used in a device for information processing, such as optical bistability/light switching, optical filtering, signal conditioning, neural networks, spatial light modulators, phaseconjugation, pattern recognition, interferometry, or the like.

Under phototransport applications, proteorhodopsins and/or bacteriorhodopsins can be used for its light-induced proton transport across a membrane, such as photovoltaic device. One such photovoltaic device is a light-driven energy generator comprising the proteorhodopsin, whereby light energy can be converted to chemical energy. The retinal analog-containing proteorhodopsins can also be used in devices for ATP generation in reactors, desalination of seawater, and/or conversion of sunlight into electricity.

Proteorhodopsins and/or bacteriorhodopsins can also be used in devices for 2D harmonic generation, radiation detection, biosensor applications, or the like.

In one embodiment, the invention provides a material suitable for an optical information carrier. Particularly, the material is suitable for optical data storage material or fraud-proof optical data carrier.

In one embodiment, the invention provides a material suitable for the storage and processing of optical information.

In one embodiment, the invention provides a material for use in storing (writing) optical data, the material being capable of retaining data while permitting nondestructive detection (reading) of such data, and being capable of reuse after optical erasure of data.

In one embodiment, the invention provides an optical information carrier material that is difficult for counterfeiters to mimic.

In one embodiment, the invention provides fraud-proof ink that changes color upon exposing to light.

Optical Information Data Carrier

The present invention provides optical information carriers that can be produced efficiently and economically and have low background noise (crosstalk), large data storage capacity, and rewriteable capacity. Such optical information carriers are effective as optical data storage material or fraud-proof optical data carriers.

The present invention provides an optical information data carrier comprising a solid material comprising an immobilized mixture of various proteorhodopsins/bacteriorhodopsins as described above, wherein said various proteorhodopsins/bacteriorhodopsins have absorption spectra that do not overlap significantly. The solid material can range in thickness from a thinly deposited layer orders of magnitude larger in two dimensions than in the third dimension to a thickly cast object with all dimensions of comparable magnitude The present invention provides an optical information carrier comprising a solid material having a immobilized mixture of various proteorhodposin/bacteriorhodopsin molecules and a substrate such as glass, paper, metal, fabric material, plastic material, wherein said solid material is deposited on said substrate. For example, the substrate is a disk, a card, or a document.

The optical information carrier of the present invention may be in the form of a thin film or membrane, which may be referred to as a two-dimensional film, or may be in the form of a thick film which may be referred to as a three-dimensional layer or block. The optical information carrier so produced includes the mixture of various proteorhodposin/bacteriorhodopsin molecules that can then be independently exposed to light of different wavelengths to convert the various molecules from a basal state to a M state.

An alkaline pH such as pH 8-12 of the optical information carrier delays the decay of the light-induced M state, stabilizing the M-state and making it possible to imprint long-lasting optical images on the PR-containing film, even at room temperature. An alkaline pH is effective for optical data storage because of longer lifetime of M-state. The desirable length of time for data storage depends on the application and can vary between a few seconds, a few minutes, a few hours, a few days, a few months, up to a few years. For fraud-proof application, short lifetime of M-state (a few seconds to several minutes) is preferred.

The solid material containing an immobilized mixture of various proteorhodopsin and/or bacteriorhodopsin molecules can be spread or sprayed on the surface of a document, a disk, and a card for use as an optical data storage material. In one embodiment, the solid material can be used in a volumetric data storage device or a holographic data storage device. A volumetric data storage device is a type of a 3D data storage device, in which a thickness of the data-recording material is divided into a number of virtual planes that each contains stored data. A volumetric data storage device is therefore comparable to a stack of 2D storage devices. A holographic data storage device is another type of 3D data storage device; it uses the thickness of the film by recording the 3D interference pattern of a data carrying and a reference light beam.

Data are written in the optical information carrier of the present invention optically by exposing specific areas of the material containing the mixture of photochromic molecules briefly to actinic light of a particular wavelength. For example, the actinic light is polychromatic yellow or green light (e.g. from a halogen lamp with a 450 nm cut-on filter), monochromatic green light (e.g. from a green Diode Pumped Solid State Frequency Doubled (DPSSFD) laser with a wavelength of 532 nm). The exposed area becomes yellow, showing that particular photochromic molecules in that area are excited by the light of a corresponding wavelength and converted to an activated M intermediate. This is the act of writing data to the solid material containing the mixture of photochromic materials. Observing the color of the different areas of the material (e.g. using a CCD) is a method of reading of the optical data written in the material.

In the absence of light, the M-state molecules gradually reverted to the basal color in about 1-2 minutes. When the M-state molecules in the excited (yellow) state are exposed briefly (less than about a second) to a reading light, for example, purple light (e.g. from a halogen lamp with a 456 nm cut-off filter) or blue light (e.g. from a blue light emitting diode (LED)), the color of the excited molecules are reverted to the basal color. This corresponds to rapid erasing of the optical signal imprinted in the film. These cycles can be repeated, thereby providing a writable, readable, erasable, and rewritable optical material. One advantage of the use of proteorhodopsin and/or bacteriorhodopsin molecules is the ability of the molecules to withstand multiple read and write cycles without photobleaching (loss of signal).

The present invention provides an optical data storage materials comprising the solid material comprising various proteorhodopsins and/or bacteriorhodopsins as described above, wherein data are written differentially by actinic light (writing light) of various wavelengths and optical signals are read differentially by reading light of various wavelengths. Optical signals are read differentially by determining the decrease of B-state molecules of each of said proteorhodopsin or bacteriorhodopsin molecule. Alternatively, optical signals are read differentially by determining the absorbance of light at the M-state maximum absorption wavelength by each of said proteorhodopsin or bacteriorhodopsin molecules.

Each of the multiple information bits within each domain is capable of being selectively written in a process induced by differing wavelengths of actinic light. Each actinic light has a wavelength that is uniquely associated with the maximum absorbance wavelength of a particular proteorhodopsin or bacteriorhodopsin molecule located within the same addressable domain. Each actinic light has a unique wavelength, which is suitable to cause predominantly only one particular proteorhodopsin or bacteriorhodopsin molecule to excite from its B-state to M-state. Accordingly, a single type of proteorhodopsin or bacteriorhodopsin molecule (a bit), which has a particular maximum absorption wavelength, is written at by an actinic light of a particular wavelength. By independently addressing each of the various proteorhodopsin and/or bacteriorhodopsin molecules, data is written independently, thus the capacity of data storage is increased due to the presence of multiple photochromic molecules in the same addressable domain.

Each of the multiple information bits within each addressable domain is also capable of being selectively read in a process induced by differing wavelengths of reading (probing) light.

One advantage to utilize a mixture of photochromic molecules is the ability to store multiple bits within the same physical space (i.e. increased density). This ability to increase the number of bits within a specific space allows for quaternary, octal or hexadecimal data storage. For example, a molecule can be in either a B or M state, represented by a 1 or a 0, which is a binary data storage scale. For each molecule, 2 bits of data are stored. The number of recording modes occupying the same addressable space is expressed as $2^n$, where n is the number of photochromic molecules that can be individually written or read. For example, the ability to put molecules with two different reading or writing wavelengths in the same addressable space allows for quaternary ($2^2$) storage. The ability to put molecules with three different reading or writing wavelengths in the same addressable space allows octal ($2^3$) storage.

In one embodiment of the invention, an optical data storage material is swept under multiple read stations, each of which has a unique wavelength of actinic light or reading light. In another embodiment of the invention, an optical data storage material is written or read simultaneously by multiple wavelengths of actinic light or reading light, each wavelength corresponds to a unique proteorhodopsin/bacteriorhodopsin molecule.

The image formed on the material such as a film can represent any kind of information that can be formed as individual data points on the molecules within the photochromic materials in the film. The larger the number of individual molecules in the photochromic mixture, the greater the optical density (O.D.), and the greater the signal of images stored therein.

The present invention provides an optical data storage device comprising one or more light sources and an optical data information carrier as described above. In one embodiment, the one or more light sources emit independently actinic writing light of different wavelengths to convert said various photochromic materials from a basal state to a M-state. In another embodiment, the one or more light sources emit reading light of different wavelengths to convert said various photochromic materials from the M-state into the basal state.

The present invention further provides a fraud-proof data carrier comprising a solid material comprising an immobilized mixture of different proteorhodopsins/bacteriorhodopsins described above, wherein said different proteorhodopsins/bacteriorhodopsins have absorption spectra that do not overlap significantly. The material containing immobilized proteorhodopsin can be spread, sprayed, solidified, printed, deposited or dried on the surface of glass, paper, fabric materials, plastic material, metal surface or mineral surface for use as a fraud-proof data carrier. The materials containing immobilized proteorhodopsin/bacteriorhodopsin molecules can also be shaped in a mold to form the three-dimensional fraud-proof data carrier.

For example, the solid material is deposited on products such as banknotes, documents, ID cards, passports, drivers' licenses, keycards, checks, securities, stickers, foils, containers, product packing materials etc., to guarantee the authenticity of the products. When proteorhodopsin/bacteriorhodopsin is exposed to light of excitation wavelength, it is excited to an activated M-state and changes to a yellow color. The color is reverted to its basal color either spontaneously with time or by exposing the material to a second light. For example, the proteorhodopsin molecule is excited by a yellow light or a green light to change color from red or purple to yellow; the color change is erased spontaneously or by illuminating the material with purple or blue light. The color change of proteorhodopsin or bacteriorhodopsin is reversible between the basal state and M-state, which provides protection against falsification. The write-read-erase cycle can be repeated multiple times without any observable change in the property of the material. Conventional inks based on pigments or organic dyes cannot mimic this color change. The color change feature makes the proteorhodopsin and/or bacteriorhodopsin containing materials difficult for counterfeiters to mimic. By using a mixture of different proteorhodopsin and/or bacteriorhodopsin molecules, multiple basal colors can be provided in the same addressable domain in security ink or documents, which makes it even more difficult to counterfeit. These different colored proteorhodopsin and/or bacteriorhodopsin molecules can be any combination of all-trans-retinal-containing proteorhodopsins, retinal analog-containing proteorhodopsins, all-trans-retinal-containing bacteriorhodopsin, and retinal analog-containing bacteriorhodopsin, as long as they have different maximum absorbance wavelengths.

Security Ink

The present invention further provides security ink comprising a mixture of different proteorhodopsins and/or bacteriorhodopsins as described above and one or more hydrophilic polymers in a liquid form; the polymers and the proteorhodopsins and/or bacteriorhodopsins form a homogeneous phase. The security ink solidifies or dries after it is applied onto a surface; and proteorhodopsins and/or bacteriorhodopsins are immobilized onto a localized region where the ink is applied to provide the security features. The security ink in general is water-based, which is dried or solidified in air and forms a film. The drying or solidification of the ink results from loss of solvent, polymerization, or curing.

The security ink is prepared by combining a mixture of proteorhodopsins and/or bacteriorhodopsins with one or more hydrophilic polymers in an aqueous solution to form a homogeneous solution. Optionally, auxiliary agents such as binders, UV absorbers or dyes are included in the security ink. Binders increase the binding or adhesion of photochromic material to the surface that the ink is applied upon. Binders useful for the present invention include gum arabic, polyvinyl acetate, polyvinyl alcohol, and polyethylene glycol. UV absorbers protect the photochromic material from UV damage and increase the UV-resistance of the security ink. UV absorbers include benzophenone, hydroxynaphthoquinone, phenylbenzoxazole, cinnamic acid esters, sulfonamide and aminobenzoic acid esters. Dyes modify the visual appearance of the ink. Other additives that may be included in the security ink are optical brighteners, driers, anti-skinning agents, thixotropy promoters, waxes, plasticizers, surfactants, defoaming agents and biocides. The hydrophilic polymers can be any water-compatible polymers in which a mixture of proteorhodopsins and/or bacteriorhodopsins can be evenly dispersed to form a homogeneous solution. Preferably, the solution containing proteorhodopsins and/or bacteriorhodopsins and the polymers can be dried in air quickly (within a minute or less) and form a film that allows efficient light absorption to excite the basal state of the photochromic materials. In one embodiment of the invention, the hydrophilic polymer is gum arabic, polyvinylalcohol, polyvinyl acetate, polyethyleneglycol or polyvinyl pyrrolidone In one embodiment of the invention, the security ink can be printed on paper, foil, glass, metal surface, or plastic.

In another embodiment of the invention, the security ink can be applied via screen-printing or ink jet printing onto a document. At ambient conditions and usual room-light illuminations, the area printed from the security ink appears, for example, purple or red color depending on the basal state of the molecules within the mixture of photochromic material. However, an increase of the light intensity would lead to a rapid change of the color to yellow (M-state). Therefore, unauthorized copies produced by digital scanning or photocopying of documents printed with security ink are easy to be distinguished from the authentic document. Conventional inks based on pigments or organic dyes cannot mimic this color change. The color change feature makes the photochromic material difficult for counterfeiters to mimic.

The following examples further illustrate the present invention. These examples are intended merely to be illustrative of the present invention and are not to be construed as being limiting.

EXAMPLES

Example 1

Temporary Data Storage

Purified bacteriorhodopsin (BR) from *Halobacterium salinarum*, mutant D96N (Zeisel and Hampp, *J. Phys. Chem.*, 1992. 96:7788-7792), 0.89 mg, was dissolved into 110 μl water with sonication. To this, 89 μl of 20% polyethyleneimine was added drop wise with vortex mixing to yield a clear purple solution. To 110 μl solution of 8 mg/ml purified proteorhodopsin mutant, Bac31A8/E108Q (U.S. Application Publication No. 2005-0095605), 89 μl of 20% polyethyleneimine was added drop wise with vortex mixing to yield a clear red solution. These two purple and read solutions were mixed together as a BR/PR PEI mixture. An immobilized gel of the BR/PR mixture was prepared by mixing 400 μl of the BR/PR PEI mixture, 246 μl of water, and 20 μl of a 2.5% solution of high molecular weight polyvinylacetate. This mixture was warmed to about 50° C. and mixed with 94 μl of a 2% solution of purified agar at 55° C. The solution was mixed on a vortex mixer and pipetted into a 1.0 ml plastic cuvette. The solution was allowed to cool to room temperature.

Figure 2:
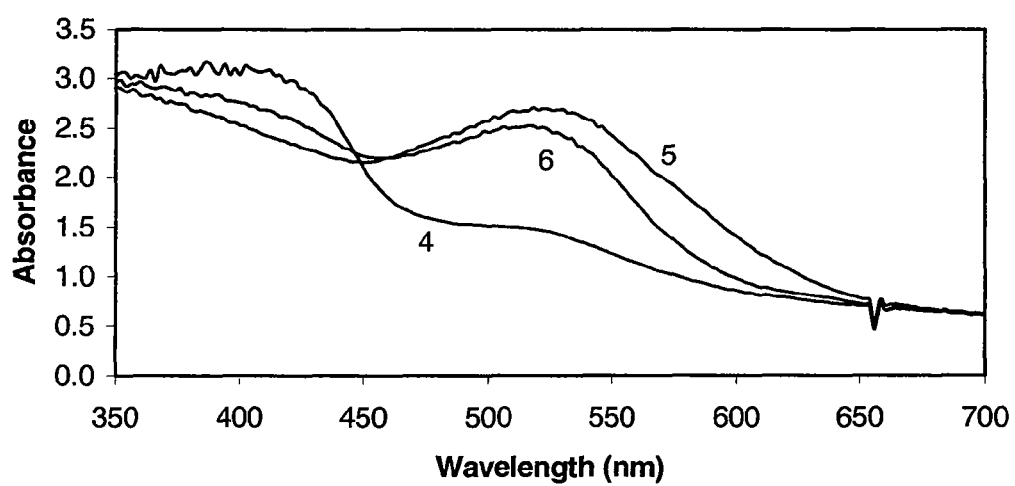
FIG. 2 shows the temporary data storage spectra of a mixture of bacteriorhodopsin and proteorhodopsin immobilized in a transparent matrix. The spectra were record in sequence following those described in FIG. 1 as described. Spectrum 4 was taken after the mixture was illuminated with a green light (510 nm). Spectrum 5 was taken after the mixture was illuminated with a violet light (400 nm). Spectrum 6 was taken after the mixture was illuminated with a violet light (400 nm), followed by a red light (640 nm).

Three small keychain LED lights having a maximum intensity at 400 nm, 510 nm, and 640 nm respectively, were used for the state switching. The cuvette containing the PR/BR gel was placed into the spectrophotometer and illuminated by the designated LED light (400 nm, 510 nm, or 400 nm followed by 640 nm) for several seconds. The designated LED light was placed over the cuvette for illumination for about 2 seconds and then removed. Spectra were then recorded on an HP 8452 Diode Array spectrophotometer in a dark room (FIGS. 1 and 2).

After the mixture containing BR and PR was illuminated with a violet light (400 nm), both BR and PR were at basal (B) state, which absorb at 570 nm and 520 nm respectively. See Spectra 1 and 5 in FIGS. 1 and 2.

Red light (640 nm) was capable of exciting BR from the B state to the M state but had no effect on exciting PR from the B sate. After the mixture containing BR and PR was illuminated with a violet light (400 nm) followed by a red light (640 nm), BR photocyled to the B state and then to the M state, and PR photocycled to the B state and remained at the B state. See Spectra 3 and 6 in FIGS. 1 and 2.

After the mixture containing BR and PR was illuminated with a green light (510 nm), both BR and PR were excited to the M state. See Spectra 2 and 4 in FIGS. 1 and 2.

A simple model to evaluate these spectra is the ratio of absorbance at 410 nm/560 nm Table 1).

TABLE 1

| Illumination sequence | $A_{410}/A_{560}$ Ratio |
| --- | --- |
| 400 nm Spectrum 1 | 1.11 |
| 510 nm Spectrum 2 | 2.59 |
| 400 nm, followed by 640 nm Spectrum 3 | 1.52 |
| 510 nm Spectrum 4 | 2.69 |
| 400 nm Spectrum 5 | 1.08 |
| 400 nm, followed by 640 nm Spectrum 6 | 1.55 |

The $A_{410}/A_{560}$ ratio can be considered a "digital state value" as described in Table 2.

TABLE 2

| Illumination sequence | Ratio 410/560 | Digital state value | Photocycle State BR | Photocycle State PR |
| --- | --- | --- | --- | --- |
| After 400 nm light | 1.1 | 0 | B | B |
| 400 nm followed by 640 nm light | 1.5 | 1 | M | B |
| After 510 nm light | 2.6 | 2 | M | M |

The data from this experiment demonstrate that a mixture containing BR and PR has the ability to temporarily encode, with light, different digital states.

The resolution of the data density that could be achieved with proper optical equipment would be expected to be no less than that for BR films as BR is the largest component (1-3μ) in the mixture. PR is monomeric (about 4-5 nm), thus PR would not be expected to affect the resolution significantly to the smallest addressable size.

Although the invention has been described with reference to the presently preferred embodiments, it should be understood that various modifications can be made without departing from the scope of the invention.

What is claimed is:

1. A security ink comprising a mixture of different photochromic materials and one or more hydrophilic polymers, wherein said photochromic materials and the hydrophilic polymers form a homogeneous liquid phase, said ink solidifies or dries after application onto a surface, thereby immobilizing said photochromic materials onto a specific location where the ink is applied, wherein said photochromic materials are two or more proteorhodopsins selected from the group consisting of all-trans retinal containing proteorhodopsins and retinal analog-containing proteorhodopsins, wherein said different photochromic materials have different maximum absorbance wavelengths.

2. The security ink according to claim 1, wherein said hydrophilic polymer is gum arabica, polyvinyl alcohol, polyvinyl acetate, polyethylene glycol or polyvinyl pyrrolidone.

3. The security ink according to claim 1, wherein said proteorhodopsins are all-trans-retinal-containing proteorhodopsins.

4. The security ink according to claim 1, further comprising auxiliary agents selected from the group consisting of binders, UV absorbers, and dyes.

5. A security ink comprising a mixture of different photochromic materials and one or more hydrophilic polymers, wherein said photochromic materials and the hydrophilic polymers form a homogeneous liquid phase, said ink solidifies or dries after application onto a surface, thereby immobilizing said photochromic materials onto a specific location where the ink is applied, wherein said photochromic materials comprise one or more bacteriorhodopsins and one or more proteorhodopsins, wherein said different photochromic materials have different maximum absorbance wavelengths.

6. The security ink according to claim 5, wherein said proteorhodopsins are selected from the group consisting of all-trans retinal containing proteorhodopsins and retinal analog-containing proteorhodopsins, and said bacteriorhodopsins are selected from the group consisting of all-trans retinal containing bacteriorhodopsins and retinal analog-containing bacteriorhodopsins.

7. The security ink according to claim 6, wherein said proteorhodopsins are all-trans-retinal-containing proteorhodopsins.

8. The security ink according to claim 6, wherein said bacteriorhodopsins are all-trans-retinal-containing bacteriorhodopsins.

9. The security ink according to claim 5, wherein said hydrophilic polymer is gum arabica, polyvinyl alcohol, polyvinyl acetate, polyethylene glycol or polyvinyl pyrrolidone.

10. The security ink according to claim 5, further comprising auxiliary agents selected from the group consisting of binders, UV absorbers, and dyes.

* * * * *